US00PP37240P2

(12) United States Plant Patent
Bourne

(10) Patent No.: US PP37,240 P2
(45) Date of Patent: Feb. 3, 2026

(54) GRAPEVINE PLANT NAMED 'SV35-5-61'

(50) Latin Name: ***Vitis* spp**
Varietal Denomination: SV35-5-61

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,685

(22) Filed: Jul. 22, 2025

Related U.S. Application Data

(60) Provisional application No. 63/732,293, filed on Jul. 31, 2024.

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Eric. C. Cole; Baker Manock & Jensen

(57) ABSTRACT

A new and distinct variety of grapevine plant named 'SV35-5-61' particularly characterized by its black colored, ovate shaped seedless berries that have a fruity flavor and which ripen in early July in the McFarland, California area.

5 Drawing Sheets

Latin name of the genus and species of the plant claimed: The plant claimed relates to a new and distinct variety of *Vitis* spp.

Variety denomination: The plant claimed shall be known as 'SV35-5-61'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of interspecific grapevine botanically known as *Vitis* spp. and hereinafter referred to as grapevine named 'SV35-5-61'. As used herein, 'grapevine' refers to all plant parts including, vines, canes, tendrils, leaves, fruit and roots of 'SV35-5-61'. Grapevine named 'SV35-5-61' is the result of an effort to produce an early-ripening, fruity seedless table grape. This new cultivar originated from a cross conducted in May 2014 near McFarland, California between female parent grapevine selection 'SV31-11-62' (unpatented) and male parent grapevine cultivar Grapevine named 'Joy' (U.S. Plant Pat. No. 25,726). Resultant ovules from the cross were harvested 42 days after pollination and cultured on 'Mccown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2014 and grown in the greenhouse at 29° C. with 12 hours illumination under high pressure sodium vapor lamps. The seedling population of 1 plant was planted in the field in the spring of 2015 near Delano, California. The new grapevine was selected on Jul. 21, 2017. It was then propagated by cuttings and grafted to 'Freedom' (unpatented) rootstock in 2018. The present invention has been found to retain its distinctive characteristics through two successive asexual propagations in 2018 and 2020 near Delano, California.

Grapevine named 'SV35-5-61' differs from its female parent grapevine 'SV31-11-62' (unpatented) by having fruit that ripens in early July in the Delano, California area while 'SV31-11-62' (unpatented) has fruit that ripens in September in the Delano, California area. Grapevine named 'SV35-5-61' has fruit with small, soft seed traces that are not noticeable when eating while the seed traces of 'SV31-11-62' (unpatented) are large and partially lignified.

Grapevine named 'SV35-5-61' differs from its male parent grapevine 'Joy' (U.S. Plant Pat. No. 25,726) by having larger berries. Additionally, clusters of grapevine named 'SV35-5-61' are very loose whereas clusters of grapevine 'Joy' (U.S. Plant Pat. No. 25,726) are well-filled.

Grapevine named 'SV35-5-61' most closely resembles commercially available grapevine 'Thomcord' (unpatented) from which it may be distinguished by its persistent green ovules within the cluster. The presence of persistent green ovules within the cluster is not a characteristic found in grapevine 'Thomcord' (unpatented).

SUMMARY OF THE INVENTION

The following are the most outstanding and distinguishing characteristics of the ripe fruit of this new variety when grown under normal horticultural practices near McFarland, California:

a. Black, ovate shaped seedless berries with fruity flavor.
b. Early ripening; and
c. Very heavy fruit production.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from a plant approximately 7 years old, grown in a field near McFarland, California in 2024.

DETAILED BOTANICAL DESCRIPTION

Figure 1:
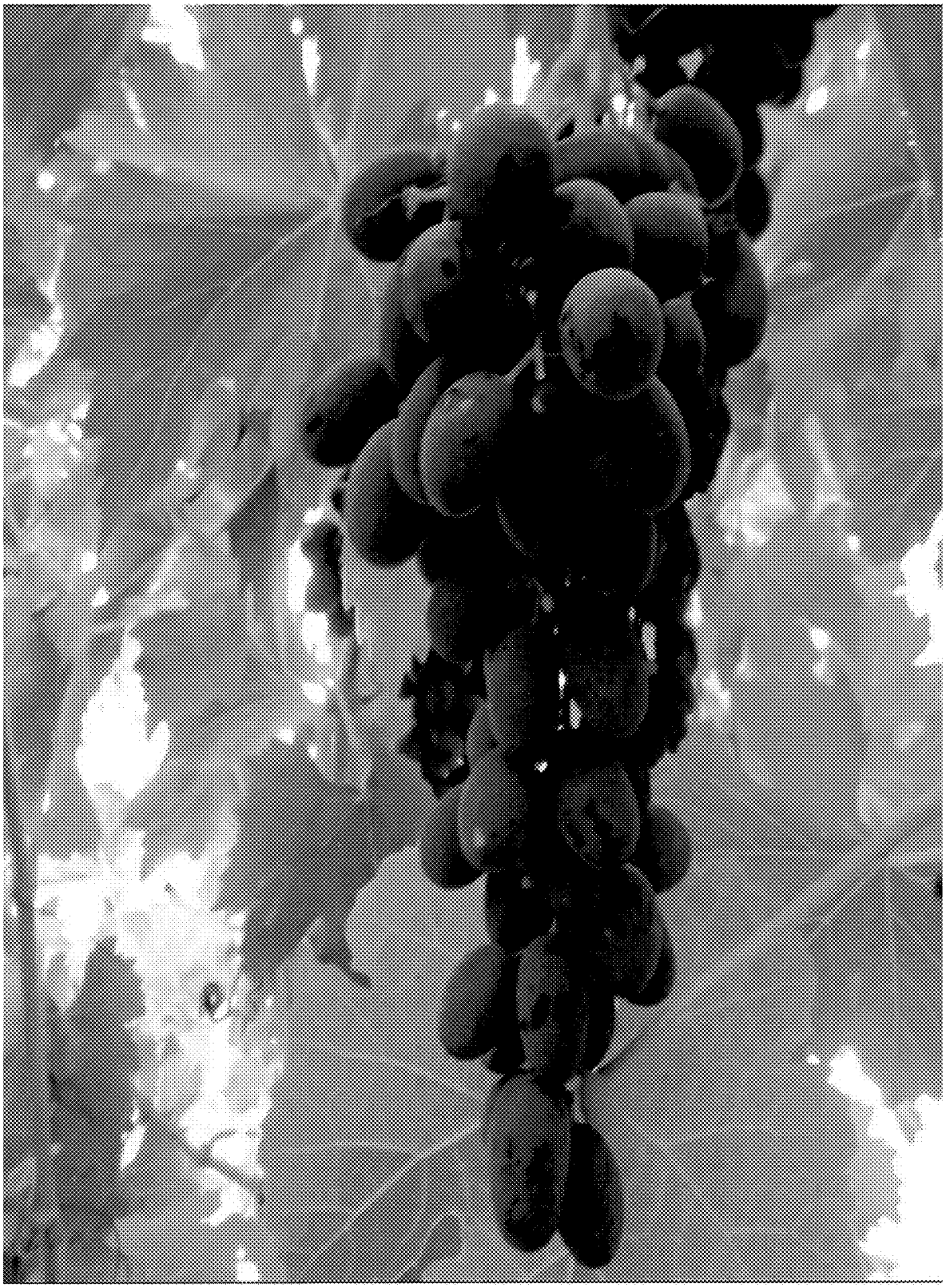
FIG. 1 Seedling vine with fruit cluster.
Figure 2:
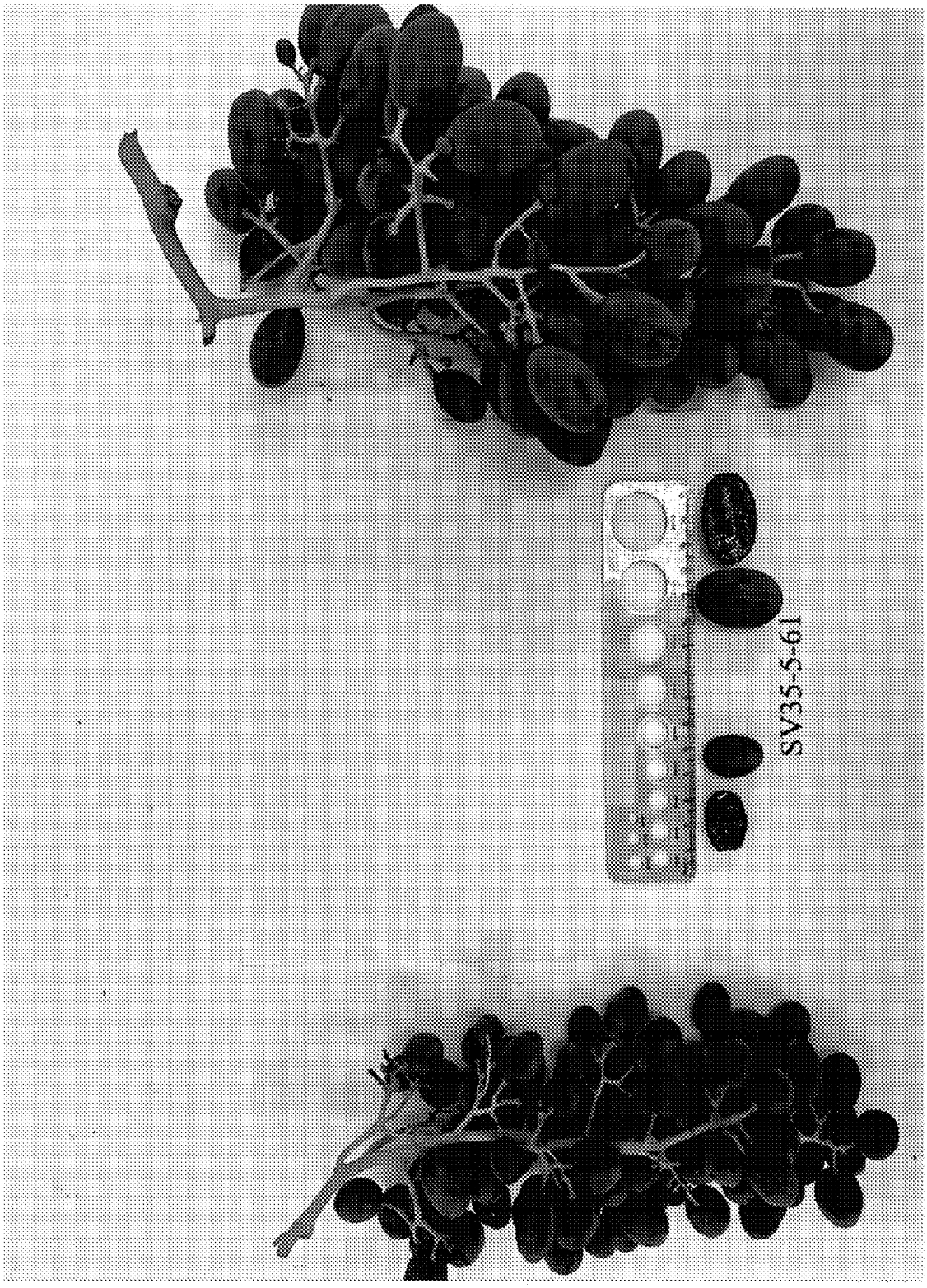
FIG. 2 Fruit cluster natural (at left) and fruit cluster treated with gibberellic acid and trunk girdling (at right).
Figure 3:
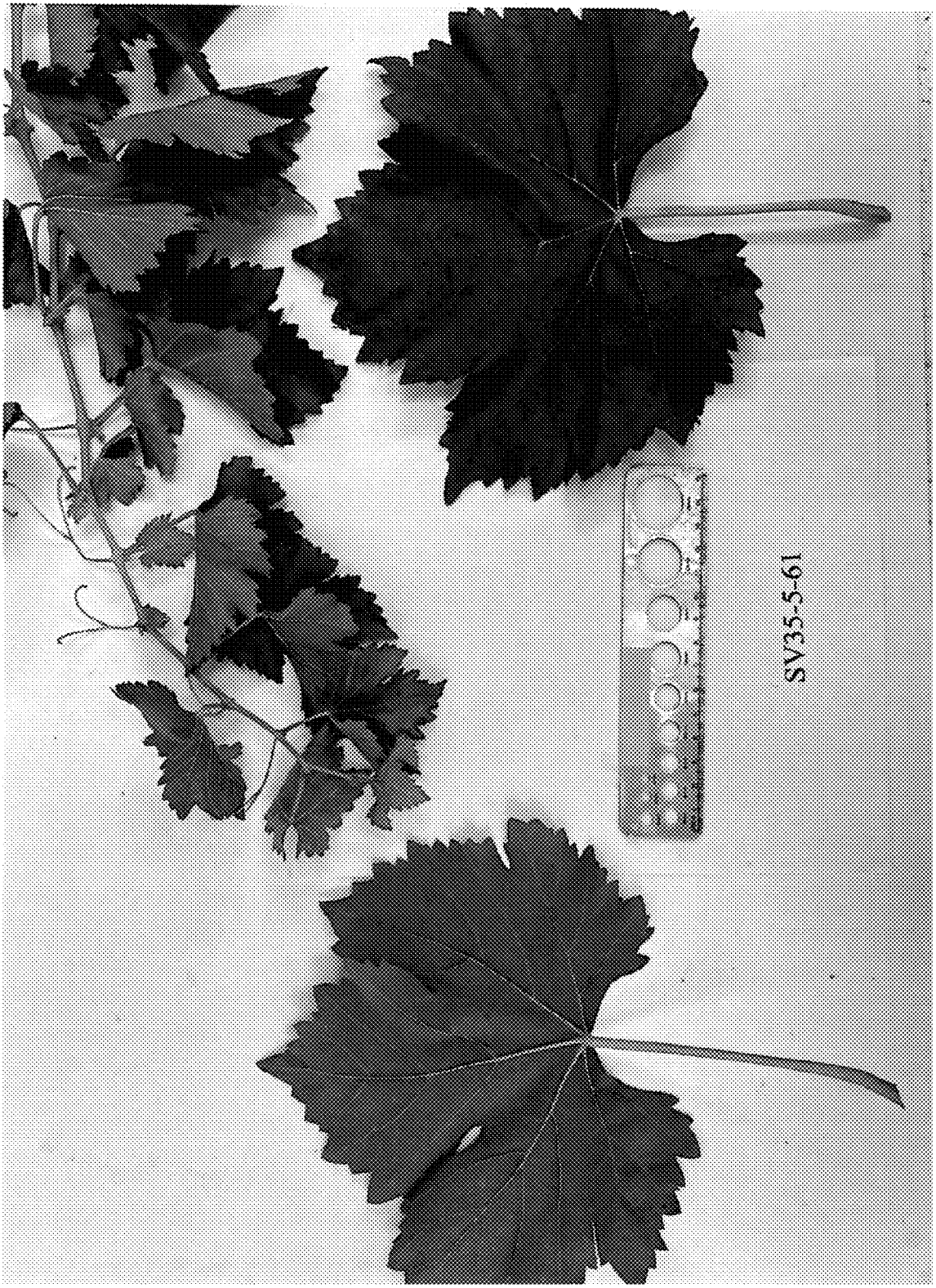
FIG. 3 Leaves and shoots.
Figure 4:
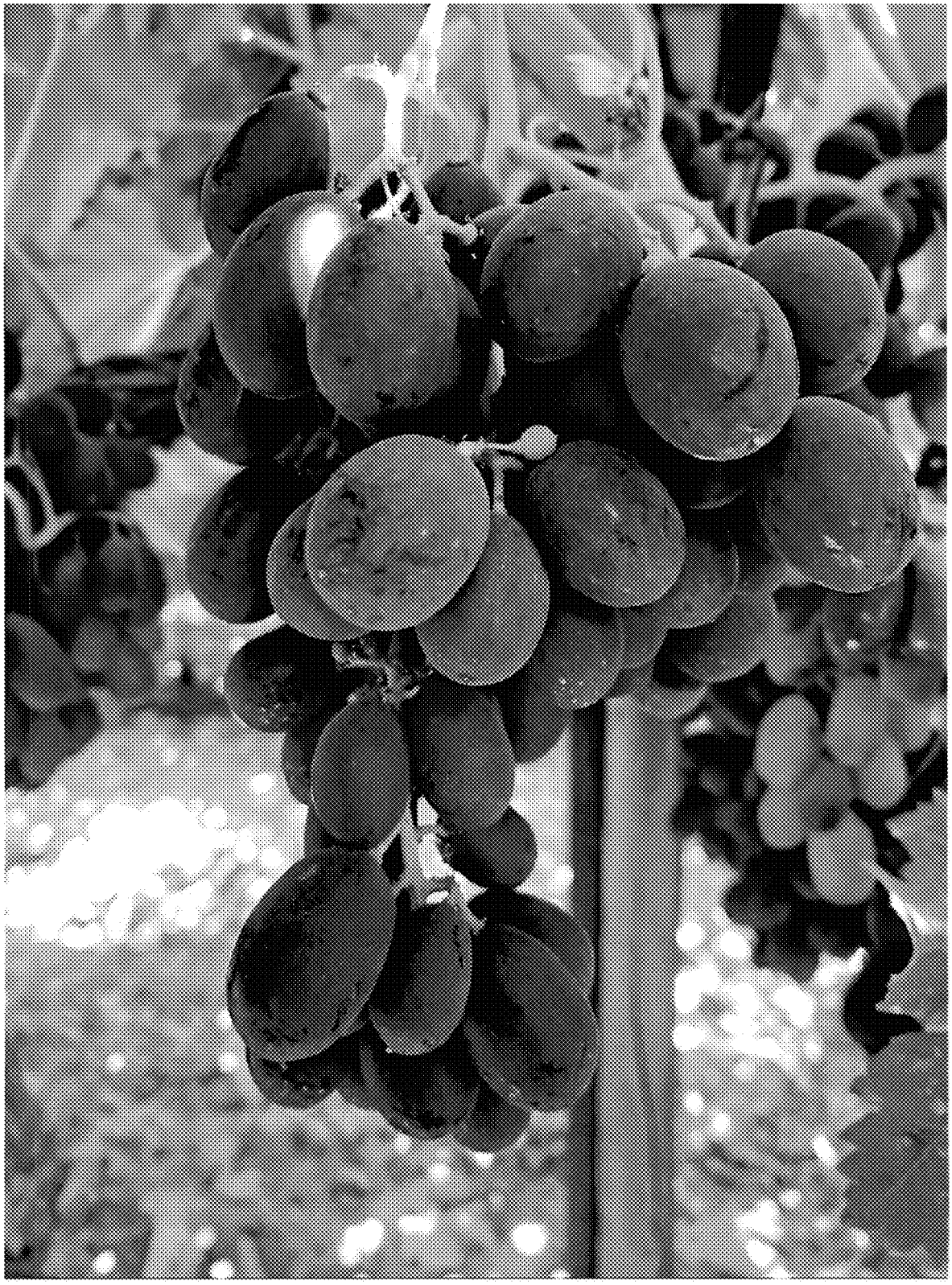
FIG. 4 Natural fruit cluster.
Figure 5:
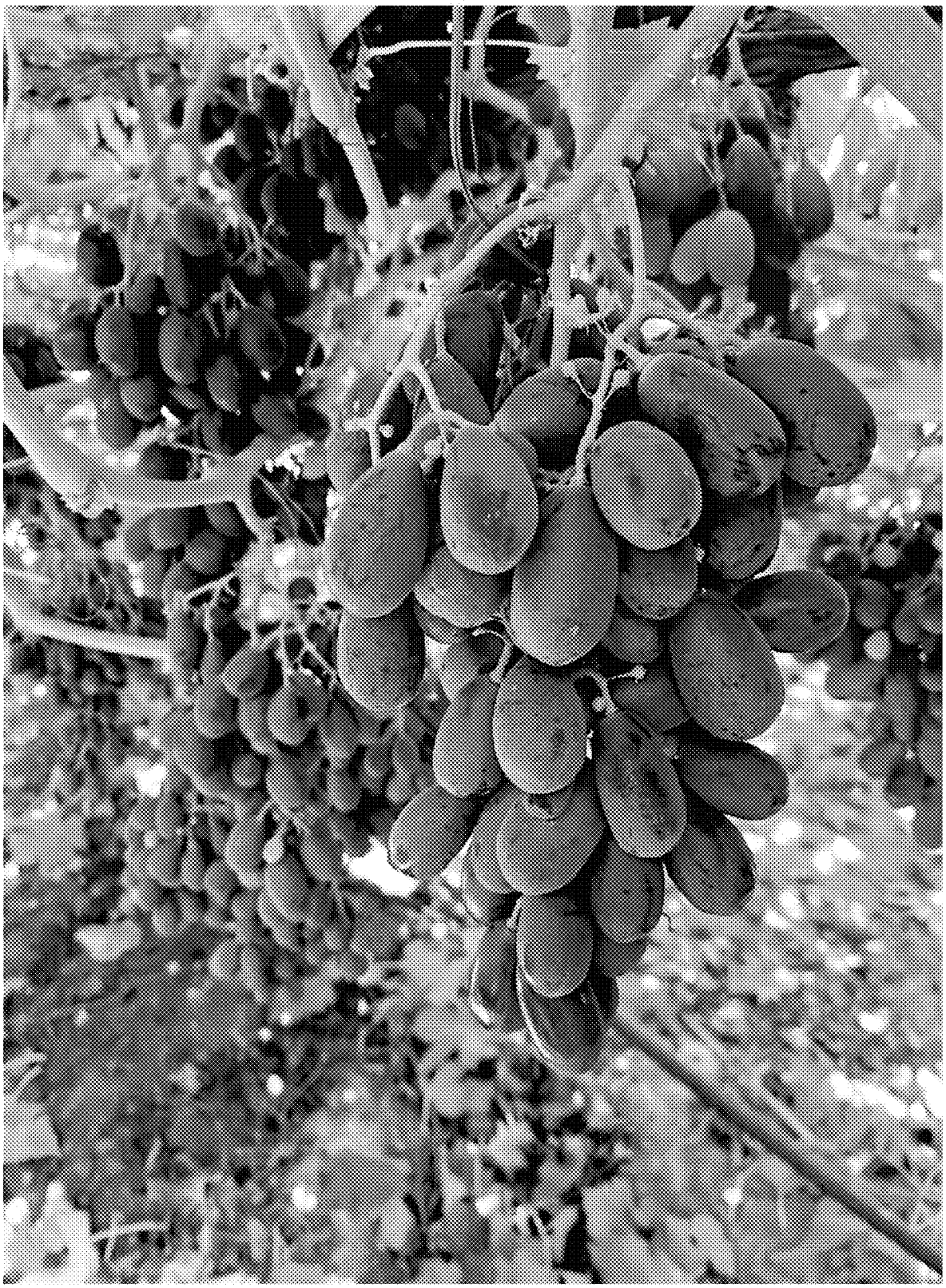
FIG. 5 Fruit cluster with exogenous gibberellic acid and trunk girdles applied.

The following detailed description sets forth the distinctive characteristics of grapevine 'SV35-5-61'. Descriptions of the new invention apply to vines of grapevine named 'SV5-5-61' grown on 'Freedom' (unpatented) rootstock at a density of 1,537 vines per hectare grown near McFarland, California in 2024. These vines were in their third year of production having been planted in 2020. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV35-5-61'.

Plant:

*Vigor*.—Vigorous; vines spur-pruned and shoot thinned to 32 shoots producing 248 cm of growth per cane.

*Density of foliage*.—Dense.

*Productivity*.—Very productive when spur pruned, up to 38, 608 kg/hectare.

*Hardiness*.—Hardiness observed to 0° C.

*Rootstock*.—'Freedom' (unpatented).

*Bud burst*.—Early.

Trunk:

*Shape*.—Broadly elliptical.

*Straps*.—Long, split.

*Surface texture*.—Shaggy.

*Trunk circumference*.—25.5 cm at 1.0 m of height.

*Inner bark color*.—RHS greyed orange group 165A.

*Outer bark color*.—RHS grey group 201A.

Mature leaves:

*Average blade length*.—16.7 cm.

*Average blade width*.—18.8 cm.

*Size of blade*.—Large.

*Shape*.—Pentagonal.

*Number of lobes*.—5.

*Anthocyanin coloration of main veins on the upper side of the blade*.—Absent.

*Mature leaf profile*.—Undulating.

*Blistering* (*upper surface*).—Absent.

*Leaf blade tip*.—Curved upward.

*Margins*.—Lobed, doubly serrate.

*Apex*.—Narrowly acuminate.

*Bases*.—Sagittate.

*Thickness*.—Medium.

*Undulation of blade between main and lateral veins*.—Slight.

*Shape of teeth*.—Both sides convex.

*Length of teeth*.—8.0 mm.

*Width of teeth*.—10.0 mm.

*Ratio length/width of teeth*.—8.0:10.0.

*General shape of petiole sinus*.—Half open.

*Tooth at petiole sinus*.—Absent.

*Petiole sinus limited by veins*.—Absent.

*Shape of upper lateral sinus*.—Closed.

*Prostrate hairs between veins* (*lower surface*).—Low density.

*Erect hairs between veins* (*lower surface*).—Medium density.

*Prostrate hairs on main veins* (*lower surface*).—Medium density.

*Density of erect hairs on main veins* (*lower surface*).—Absent.

*Prostrate hairs on main veins* (*upper surface*).—Medium density.

*Upper surface*.—Summer color: RHS yellow-green group 147A. Surface texture: Smooth. Surface appearance: Dull. Goffering of blade: Absent.

*Lower surface*.—Summer color: RHS yellow-green group 146A. Anthocyanin coloration of main veins on lower leaf surface: Absent. Anthocyanin coloration on laterals: Absent. Glossiness: Low. Pubescence: Absent. Surface texture: Rough. Surface appearance: Dull.

*Petiole*.—Length: 14.0 cm. Length of petiole compared to middle vein: About equal. Density of prostrate hairs: Absent. Density of erect hairs: Absent. Shape of base of petiole sinus: Sagittate. Color: In shade: RHS yellow-green group 144C. In sun: RHS yellow-green group 144B.

Tendrils:

*Number and pattern*.—Bifurcated and trifurcated; Continuous after 5th node.

*Length*.—30.0 cm.

*Diameter*.—3.6 mm.

*Texture*.—Smooth.

*Color*.—RHS yellow-green group N144A.

Growing tips (young shoot):

*Pubescence*.—Present, prostrate.

*Color*.—RHS yellow-green group 144A.

*Anthocyanins*.—Absent.

*Shape*.—Rounded.

*Apex*.—Fully open.

*Shoot attitude*.—Semi-erect.

*Prostrate hairs on the tip of young shoot*.—Very sparse.

Green summer shoots:

*Internode color upper surface*.—RHS yellow-green group 144B.

*Internode color lower surface*.—RHS yellow-green group 144C.

*Node color upper surface*.—RHS yellow-green group 144B.

*Node color lower surface*.—RHS yellow-green group 144B.

*Density of erect hairs on internodes*.—Absent.
*Internode length*.—11.2 cm.
*Width at node*.—15.9 mm.
*Main color*.—RHS greyed-orange group 165C.

Woody shoot:
*Canes*.—Shape: Broadly elliptical. Internode length: About 11.2 cm. Width at node: 22 mm. Surface: Smooth. Main color: RHS greyed orange group 165B. Lenticels: Inconspicuous.
*Buds*.—Shape: Slightly pointed. Cane bud fruitfulness: Basal buds fruitful, usually 2 clusters per shoot Length: 5.9 mm. Width: 5.3 mm. Height: 4.3 mm. Color: RHS greyed orange group 166A.

Flowers:
*Flower sex*.—Perfect.
*Position of first flowering nodes*.—Usually the 4th node.
*Number of inflorescences per shoot*.—2.
*Flower cluster width*.—9 cm.
*Flower cluster length*.—28.5 cm.
*Cluster stem color*.—RHS Yellow green group 144B.
*Calyptra color*.—RHS yellow-green group 144A.
*Ovary length* (*mm*).—2 mm.
*Ovary width* (*mm*).—1 mm.
*Ovary color*.—RHS Green group 137C.
*Filament length*.—2 mm.
*Filament color*.—RHS Yellow green group 145B.
*Anther length* (*mm*).—1 mm.
*Anther color*.—RHS Yellow group 9C.
*Date of full bloom*.—May 13, 2024.

Fruit:
*Ripening period*.—Early season at McFarland, California.
*Date of ripening*.—Jul. 18, 2022 at McFarland, California.
*Use*.—Fresh market.
*Keeping quality*.—Very good.
*Shipping quality*.—Very good.
*Solids-sugar*.—20 brix at full maturity.
*Total acidity*.—0.69.
*PH*.—3.46.
*Cluster*.—Size: Medium. Length (peduncle excluded): 21.3 cm. Width: 13.0 cm Weight: Natural, without gibberellic acid treatment: 286 g. With gibberellic acid treatment: 971 g. Density: Very loose. Number of berries: 107. Form: Conical.
*Peduncle*.—Length: 2.7 cm. Lignification: Slight. Color: RHS yellow green group 144A.
*Berry*.—Size: Large. Uniformity of size: Uniform. Weight Natural, without gibberellic acid treatment: 5.3 g. With gibberellic acid treatment: 8.3 g. Shape: Natural, without gibberellic acid treatment: Elliptic. With gibberellic acid treatment: Obovate. Presence of seeds: Seedless; most berries develop one or two small, soft rudimentary seeds less than 1.0 mm in length. Cross section: Circular. Dimensions: Longitudinal axis: 2.14 cm. Horizontal axis: 1.69 cm. Skin color (without bloom): RHS Black group 202A. Coloration of flesh: RHS Yellow green group 145B. Juiciness of flesh: Very juicy. Juice color: RHS Red purple group N74D. Berry firmness: Firm, not crisp. Berry flavor: Fruity, a mixture of foxy and vinifera, non-muscat flavors. Bloom (cuticular wax): Strong. Pedicel length: 1.1 cm. Berry separation from pedicel: With difficulty; vascular traces well-developed.
*Skin*.—Thickness: Medium. Texture: Crisp. Reticulation: Absent. Roughness: Absent. Tenacity: Tenacious to flesh. Tendency to crack: Resistant.

Disease and insect resistance: Grapevine plant named 'SV35-5-61' is known to be susceptible to powdery mildew of grapevine, *Erysiphe necator* Schwein. Standard commercial control measures for powdery mildew are adequate for complete control of this disease. No other diseases or insect pests have been observed on this grapevine plant named 'SV35-5-61' under growing conditions in the McFarland, California area.

Having thus described and illustrated my new variety of grapevine, I claim:

1. A new and distinct variety of grapevine plant named 'SV35-5-61', substantially as illustrated and described herein.

* * * * *